United States Patent [19]

Privalov et al.

[11] 4,070,409
[45] Jan. 24, 1978

[54] PROCESS FOR RECOVERING ANTHRACENE

[76] Inventors: Vasily Efimovich Privalov, ulitsa Galana, 5, kv. 13; Evgeny Iosifovich Vail, ulitsa Tobolskaya, 52, kv. 36; Larisa Semenovna Kuznetsova, pereulok Avtostradny, 10, kv. 1; Konstantin Alexeevich Belov, ulitsa Frunze, 15, kv. 6; Ivan Mikhailovich Nosalevich, ulitsa Sumskaya, 124-a, kv. 17; Igor Vasilievich Romanov, prospekt Gagarina, 7, kv. 107, all of Kharkov, U.S.S.R.

[21] Appl. No.: 699,966

[22] Filed: June 25, 1976

[51] Int. Cl.$^2$ ............................................. C07C 15/28
[52] U.S. Cl. ..................................... 260/675; 208/328
[58] Field of Search ................. 260/318, 675; 208/328

[56] References Cited

U.S. PATENT DOCUMENTS

| 2,183,852 | 12/1939 | Boyd | 208/323 |
|---|---|---|---|
| 2,783,287 | 2/1957 | Nickolls et al. | 260/675 |

FOREIGN PATENT DOCUMENTS

| 819,125 | 3/1958 | United Kingdom | 260/675 |

*Primary Examiner*—Herbert Levine
*Attorney, Agent, or Firm*—Haseltine, Lake & Waters

[57] ABSTRACT

A process for recovering anthracene from crude anthracene, which comprises treatment of crude anthracene with an aprotic bipolar solvent N,N-dimethylacetamide. After such treatment suspension I is obtained which is separated into liquid and solid phases. The solid phase is treated with N,N-dimethylacetamide at a temperature within the range of from 52° to 135° C to give suspension II containing impurities which are insoluble in the solvent employed. These impurities are separated from said suspension II, while the remaining solution is cooled to a temperature within the range of from −10° to +40° C to give suspension III containing crystals of anthracene. The resulting crystals are separated from the suspension.

The process according to the present invention makes it possible to recover anthracene from crude anthracene with a yield of from 76.6 to 80%. Purity grade of the final product, as to the content of anthracene, is 97.2 to 98.9%. The process is rather simple in respect of the employed technology.

2 Claims, No Drawings

PROCESS FOR RECOVERING ANTHRACENE

The present invention relates to processes for recovering anthracene.

Anthracene is useful in various branches of industry.

Thus, it is employed in chemical industry for the production of anthraquinone, alizarine and indanthrene dyes which are at present the most widely used dyes ensuring a wide color range. The highest-purity anthracene is used in the preparation of monomers for obtaining products with a whole spectrum of valuable properties. Such products feature a high thermal stability, radiation-stability and can be operated within a wide range of temperatures; they also possess a considerable resistance to thermal shocks and sign-alternating temperature loads.

Anthracene also represents a valuable raw material for the production of special-purpose lubricants.

A high-purity anthracene of coal-tar origin as well as synthetic anthracene are efficiently used in special application fields such as scintillation technology.

Commercially employed anthracene contains mineral impurities, small amounts of phenanthrene, carbazole as well as higher molecular weight products (chrysene, benzopyrene and the like).

The presence of said impurities in anthracene substantially impairs the quality of products obtained therefrom and considerably complicates the process for producing same. Thus, carbazole impurities in an amount of above 3% by weight result in complication of the commercially employed process for producing anthraquinone by vapor-phase catalytic oxidation of anthracene and do not provide for the required quality of the final product. This is attributable to the fact that at operation temperatures carbazole gives condensation products of the imino group (dicarbazides and resinous products). Said resinous impurities impair the activity of catalysts by blocking active centers thereof and result in clogging of the evaporator pipes. Decomposition products of said resinous substances (which comprise a porous carbonaceous deposit) reduce the thermal conductivity coefficient of the evaporator walls, whereby optimal conditions of the process become distorted.

Phenanthrene, carbazole and high-molecular weight impurities resulting from oxidation in this process result in strongly undesirable contaminants in the desired products (quinones of different structure, anhydrides and polycarboxylic acids).

Mineral inorganic impurities result in clogging of nozzles and pumps; they are often sintered with carbonaceous products of carbazole decomposition and partially are included in the final commercial product.

Known in the art is a process for recovering anthracene from crude anthracene. The latter comprises an intermediate product in the process of recovering anthracene from coal-tar. This crude anthracene contains anthracene, carbazole, phenanthrene-basic components as well as smaller amounts of naphthalene, fluorene, fluoranthene, diphenylene oxide, brazane, chrysene, pyrene, tetracene, benzopyrene and some high-molecular weight unidentified products. Furthermore, crude anthracene is contaminated with mineral impurities, oils (mixtures of aromatic hydrocarbons) and water.

The process comprises treating crude anthracene with acetone at a temperature of the order of 50° C. The weight between the crude anthracene and the acetone is 1:3–5 respectively. In doing so, phenanthrene, carbazole and other impurities contained in the anthracene are dissolved in the acetone. As a result, a suspension of crude anthracene in acetone is obtained. The solid phase is recovered from the suspension by centrifugation. The resulting solid product is charged into another vessel provided with a stirrer, whereafter acetone is added (weight ratio between the solid product and acetone is 1:3 respectively). After vigorous stirring at the temperature of 50° C a suspension is again produced. During the process of preparing this suspension the impurities contained in anthracene are further dissolved.

The solid phase is recovered from the suspension by centrifugation. The stages of treating solid phases with acetone and recovering the solid product are repeated three more times. As a result, enriched anthracene is recovered which is washed with a solvent and dried to give a commercial product with a content of anthracene of 93–93.5% by weight.

This prior-art process has a principal disadvantage in that anthracene is recovered in an insufficient yield. The recovered anthracene has an insufficient purity grade (thus, in the production of anthraquinone anthracene should contain at least 96% by weight of the principal substance). Among contaminants incorporated in the final product are mineral impurities, phenanthrene, carbazole, and products with a higher molecular weight than anthracene. Furthermore, in the practice of this process large amounts of solvent are consumed along with an increased heat consumption for regeneration of the solvent due to the use of great amounts thereof.

It is an object of the present invention to provide a process of recovering anthracene from crude anthracene which would make it possible to obtain anthracene with a higher purity grade and in a higher yield.

This and other objects of the present invention are accomplished by a process, wherein crude anthracene is treated with a bipolar aprotic solvent to give suspension I which is then separated into liquid and solid phases, followed by treating the resulting solid phase with the solvent employed for the treatment of said crude anthracene. In accordance with the present invention, the bipolar aprotic solvent is N,N-dimethylacetamide and the treatment of the solid phase with this solvent is effected at a temperature within the range of from 52° to 135° C to give suspension II containing impurities which are insoluble in the solvent; said impurities are separated from said suspension II and the remaining solution is cooled to a temperature of from −10° to +40° to give suspension III containing crystals of anthracene which are then recovered from this suspension.

The crude anthracene used can be, for example, crude anthracene resulting from coal-tar processing in the coal-tar chemical industry. As has been mentioned hereinabove, such crude anthracene contains the principal component in an amount of from 15 to 80% by weight, as well as carbazole, phenanthrene as basic impurities, and oils, water and mineral compounds.

Crude commercial anthracene prepared synthetically can also be used. This anthracene contains polyhalobenzenes and products with a higher molecular weight than anthracene. It is also possible to employ pre-purified crude anthracenes of both the former and the latter origin.

In the treatment of crude anthracene with the solvent according to the present invention, washing of solid crystalline anthracene contaminated with the above-mentioned impurities and oils takes place. At the above-mentioned temperatures substantial amounts of the basic impurities are dissolved in the solvent according to the present invention, whereas in the case of using less selective solvents elevated temperatures must be employed. Thus, in case of acetone the process temperature is 50° C (i.e. temperature approaching the boiling point of acetone), Furthermore, it is necassary to use great amounts of the solvent (3-5-fold of the crude anthracene weight). N,N-Dimethylacetamide is superior to other solvents of the bipolar aprotic series and acetone, in particular in that at moderate temperatures (15° to 40° C) it but sparingly dissolves the principal product (anthracene) and easily dissolves such impurities as carbazole, phenanthrene and the like.

The high dissolving power of N,N-dimethylacetamide makes it possible to employ small amounts of the solvent, ensuring therewith a sufficient process effectiveness at this stage. It is quite sufficient to employ the components at the following weight ratio between the solvent and crude anthracene of 0.7-1.5:1 respectively.

As has been mentioned hereinbefore, the process at this stage can be conducted at ambient temperature (15° to 40° C). At lower temperatures, it will take a longer time period to carry out this stage, whereas at higher temperatures anthracene begins to dissolve.

At elevated temperatures (within the range of from 52° to 135° C) the dissolving power of N,N-dimethylacetamide for anthracene sharply increases. This enables, in subsequent operations of crystallization and recrystallization, the use of a minimal amount of the solvent.

Upon dissolution of the solid phase separated from the suspension I, suspension II is obtained which contains mechanical and mineral impurities (solid phase) insoluble in the solvent. Due to the use of the solvent according to the present invention within said temperature range, there is an opportunity of separating mechanical impurities at this stage of the process. This stage of recrystallization is much more effective for the whole process of recovering anthracene than a gradual multistage elution of the impurities through the pores and surface of the solid finely divided crude product in the prior-art process of recovering anthracene by means of acetone.

The use of N,N-dimethylacetamide at a temperature within the range of from 52° to 135° C at the stage of treatment of the solid phase resulting from separation of suspension I makes it possible to completely dissolve the solid product (except the insoluble impurities). These temperatures are substantially lower than the boiling point of the solvent. The use of acetone at this stage even in great amounts thereof necessitates application of an excess pressure (4 to 10 atm.g.) and conducting the process in an autoclave. The solvent amount and temperature at this stage are selected as a function of the anthracene content in the starting material (the higher the anthracene content, the higher the weight ratio between the solid product and the solvent and the higher the temperatures applied).

The following stage of anthracene crystallization is conducted using the solution obtained after separation of mechanical and mineral impurities from suspension II by way of cooling this solution to a temperature of from 15° to 40° C. In the case of a high content of anthracene in the starting material (and accordingly a small amount of impurities) and in the case of a more complete recovery of anthracene, cooling of the solution is conducted to a lower temperature ($-10°$ to $+14°$ C). As a result, suspension III is obtained, wherefrom the solid phase is isolated which comprises crystals of purified anthracene. The resulting crystals are washed with the solvent and dried.

In order to produce anthracene with a higher purity grade, the resulting crystals of anthracene should be dissolved, at a temperature within the range of from 52° to 135° C, in N,N-dimethylacetamide, and it is advisable that the thus-prepared solution be cooled to a temperature ranging from $-10°$ to $+40°$ C. An appropriate temperature is selected as a function of the desired product yield and the requirements as to its purity grade. The weight ratio between the solvent and crystalline product at this stage should be equal to 1.0-3:1. The solvent amount, with the account of temperature, in this case is selected proceeding from the same considerations as in the last stage of dissolving the solid anthracene-containing product.

To obtain a more pure product, it is necessary to maintain a higher temperature (within the above-indicated temperature range) so that maximal amounts of the impurities would remain in the mother liquor (the desired product yield is, naturally, somewhat decreased therewith); the same occurs with the use of higher amounts of the solvent. As a result of cooling, suspension IV is obtained containing crystals of the purified anthracene, which are then recovered.

The solvent, viz., N,N-dimethylacetamide, selected from the class of bipolar aprotic solvents appears to have a higher selectiveness for the process of anthracene separation from crude anthracene as compared to acetone, N,N-diemthylformamide and N-methylpyrrolidone. Furthermore, the solvent of the present invention is superior to the two latter solvents in its higher stability after repeated use in the technological cycle (including the regeneration process; the solvent of the mother liquor is generally distilled off under vacuum). N,N-Dimethylacetamide easily dissolves the principal contaminant components (carbazole, phenanthrene) at moderate temperatures (15° to 40° C) and but very slightly dissolves anthracene within the same temperature range. This makes it possible to substantially reduce the solvent amount, to lower the treatment temperature for crude anthracene and to reduce the duration of this stage as compared to the prior-art process employing acetone as the solvent.

The solvent according to the present invention has a higher boiling temperature (154° to 156° C) than acetone (56.24° C). This substantially decreases the solvent losses in all the stages of the process and makes it possible to dissolve partially purified crude anthracene in a minimal amount of the solvent at a temperature within the range of from 52° to 135° C without applying excess pressure or using any special equipment.

At elevated temperatures (52° to 135° C) N,N-dimethylacetamide easily dissolves anthracene. This enables crystallization of anthracene under atmospheric pressure for the purification of anthracene from mineral and mechanical impurities. This is impossible in the prior-art process contemplating the use of acetone as the solvent. The crystallization and recrystallization technique is a more effective process of anthracene concentration than extraction under the liquid-solid phase conditions as used in the prior-art method involving the use of acetone as the solvent.

Therefore, the process according to the present invention makes it possible to recover anthracene from the starting crude anthracene with a higher yield as compared to the prior art process (76.6–80% by weight of the content in crude anthracene comparing to 50% in the case of using acetone). The final product also features a higher purity grade (the principal product content is 97.2 to 98.9%). Insignificant content of impurities in the final product practically exerts no detrimental effect on the quality of products made from this anthracene.

The process according to the present invention does not necessitate the use of large amounts of the solvent. This, in turn, makes it possible to reduce energy consumption for preheating and regeneration of the solvent.

The process for recovering anthracene according to the present invention is rather simple and practically embodied in the following manner.

Crude anthracene is charged into a flask provided with a stirrer, a thermometer and a reflux condenser and N,N-dimethylacetamide is added thereto (the weight ratio between crude anthracene and N,N-dimethylacetamide is equal to 0.7–1.5:1 respectively). The resulting mass is stirred at a temperature ranging from 15° to 40° C to give, as a result, suspension I which is then separated into liquid and solid phases. Therewith, contained in the liquid phase are 10–15% by weight of oils, 5–10% by weight of water.

A solid crystalline residue is mixed with a fresh portion of the solvent in the weight ratio between said residue and the solvent equal to 1:0.7–1.5 and heated to a temperature within the range of from 52° to 135° C to give suspension II containing mineral and mechanical impurities as the solid phase. This solid phase is removed from the suspension by conventional techniques such as filtration, centrifugation and the like. The filtrate is cooled to a temperature within the range of from −10° to +40° C. Such cooling results in the preparation of suspension III containing crystals of purified anthracene. The precipitated crystals are separated from the mother liquor, washed with N,N-dimethylacetamide and dried, for example, in vacuum under a residual pressure of from 10 to 20 mm Hg and at a temperature within the range of from 70° to 80° C.

The mother liquor can be used for the treatment of crude anthracene in the first stage of the process. The used solvent is then subjected to regeneration.

As a result of such treatment of crude anthracene pure anthracene is obtained containing the principal product in the amount of 97.2 to 97.98% by weight. The yield of anthracene from crude anthracene is 73.6 to 80% as calculated for a 100% product.

In order to obtain anthracene with a higher purity grade, the resulting crystals of anthracene are again treated with N,N-dimethylacetamide at the weight ratio between the crystalline product and the solvent of 1:1–1.5 at a temperature within the range of from 52° to 135° C. As a consequence, a solution is obtained which practically contains no impurities; this solution is cooled to a temperature within the range of from −10° to +40° C to give suspension IV, wherefrom purified anthracene crystals are separated, followed by washing and drying thereof to obtain anthracene with the principal product content of from 98.2 to 98.9% by weight.

EXAMPLE 1

Into a round-bottom flask provided with a stirrer, 1 kg of crude anthracene (contains 25% by weight of anthracene, 20% by weight of phenanthrene, 18% by weight of carbazole) and 1 kg of N,N-dimethylacetamide are charged. The flask contents are thoroughly stirred at ambient temperature (15° C). As a result, a suspension is obtained, wherefrom the solid phase is separated by filtration. The resulting solid product is placed into a flask provided with a stirrer, a thermometer and a reflux condenser, whereafter 1 kg of N,N-dimethylacetamide is added thereto. The resulting mass is heated till complete dissolution of the solid product 52° C). The thus-prepared solution is filtered through a hot-filtration funnel to remove mineral and mechanical impurities. The remaining mother liquor is cooled to the temperature of 25° C; in so doing, crystals are precipitated which are separated from the liquid phase by filtration. The crystals comprise enriched crystalline anthracene. These crystals are washed with the solvent (N,N-dimethylacetamide) and dried in vacuum under a residual pressure of 10 mm Hg and at a temperature of 60° C. The resulting dry product contains 97.2% by weight of anthracene, which amounts to 189.2 g or, as calculated for a 100% product, 73.6% of the anthracene content in the crude product.

Anthracene content in the resulting product is determined by way of oxidation of anthracene to anthraquinone and determination of the latter by the gravimetric method. As it is known, this method (as compared to the others) gives somewhat undervalued results (1–1.2%).

Carbazole content is determined indirectly via nitrogen (Kjeldahl method). It should be taken into account that upon recrystallization of anthracene from N,N-dimethylacetamide the latter is contained in anthracene crystals in an amount of from 0.7 to 1.0% by weight. To obtain a more accurate result of the content of carbazole, the resulting product (anthracene) should be washed, prior to the determination of nitrogen content, in a neutral solvent to remove traces of N,N-dimethylacetamide.

EXAMPLE 2

Into a round-bottom flask provided with a stirrer, 1 kg of pre-enriched crude anthracene (containing 40% by weight of anthracene, 8% by weight of phenanthrene and 10% by weight of carbazole) and 0.7 kg of N,N-dimethylacetamide are charged. The flask contents are thoroughly stirred at ambient temperature (15° C). As a result, a suspension is obtained, wherefrom the solid phase is separated by centrifugation and washed with the solvent to give a solid product (containing 93.2% by weight of anthracene). This solid product is placed into a flask provided with a stirrer, a thermometer and a reflux condenser and then 1 kg of N,N-dimethylacetamide is added thereto. The resulting mass is heated to complete dissolution of the solid product (135° C). The thus-prepared solution is filtered through a hot-filtration funnel to remove mechanical and mineral impurities. The remaining mother liquor is cooled to the temperature of 40° C; in doing so, crystals are precipitated which are separated from the liquid phase by centrifugation. These crystals comprise crystalline anthracene. They are washed with the solvent (N,N-dimethylacetamide) and dried at a temperature of 100° C under a residual pressure of 50 mm Hg. The resulting dry product contains 97.98% by weight of anthracene, which amounts to 326 g. This corresponds, as calculated for a 100% product, to 80 % of the content of anthracene in the starting crude product. The mother liquor resulting from this stage can be used for the treatment of crude anthracene in the first stage of the process.

Methods of quantitative analysis of anthracene anf carbazole are similar to those described in the foregoing Example 1.

EXAMPLE 3

A product is prepared in a manner similar to that described in Example 2 hereinabove. 1 kg of the product is charged into a flask provided with a stirrer, a thermometer and a reflux condenser, whereafter it is treated with 1 kg of N,N-dimethylacetamide poured into the flask. The flask contents are heated to complete dissolution of the solid product (135° C). The thus-prepared solution is cooled to the temperature of 40° C; as a consequence, crystals are precipitated which are separated from the liquid phase by centrifugation. The crystalline product comprises anthracene. It is washed with the solvent (N,N-dimethylacetamide) and dried in a manner similar to that described in the foregoing Example 2. The resulting dry product contains 98.8% by weight of anthracene. The yield of anthracene, as calculated for a 100% product, is 97.2% by weight of the anthracene content in the starting crude product employed in the experiment.

Methods of quantitative analysis of anthracene and carbazole are similar to those described in Example 1 hereinbefore.

What is claimed is:

1. A process for recovering anthracene from crude anthracene, comprising treating crude anthracene with N,N-dimethylacetamide to give suspension I; separating the suspension I into liquid and solid phases; treating the solid phase with N,N-dimethylacetamide at a temperature ranging from 52° to 135° C to give suspension II containing impurities insoluble in the solvent; separating said impurities from suspension II; cooling the remaining solution from suspension II to a temperature ranging from −10° to +40° C to give suspension III containing anthracene crystals; separating the crystals of anthracene from said suspension III.

2. A process as claimed in claim 1, wherein the separated anthracene crystals are treated with N,N-dimethylacetamide at a temperature ranging from 52° to 135° C to give a solution; cooling said solution to a temperature ranging from −10° to +40° C to give suspension IV containing anthracene crystals; recovering said anthracene crystals from said suspension IV.

* * * * *